US012066437B2

(12) United States Patent
Kulpakko

(10) Patent No.: US 12,066,437 B2
(45) Date of Patent: Aug. 20, 2024

(54) **METHOD FOR DETERMINING *ESCHERICHIA COLI***

(71) Applicant: AQSENS HEALTH OY, Turku (FI)

(72) Inventor: Janne Kulpakko, Turku (FI)

(73) Assignee: AQSENS HEALTH OY, Turku (FI)

( * ) Notice: Subject to any disclaimer, the term of this patent is extended or adjusted under 35 U.S.C. 154(b) by 548 days.

(21) Appl. No.: 17/290,566

(22) PCT Filed: Oct. 17, 2019

(86) PCT No.: PCT/FI2019/050742
§ 371 (c)(1),
(2) Date: Apr. 30, 2021

(87) PCT Pub. No.: WO2020/089512
PCT Pub. Date: May 7, 2020

(65) Prior Publication Data
US 2021/0373016 A1  Dec. 2, 2021

(30) Foreign Application Priority Data

Nov. 1, 2018 (FI) ...................................... 20185927

(51) Int. Cl.
*G01N 33/569* (2006.01)
(52) U.S. Cl.
CPC . *G01N 33/56916* (2013.01); *G01N 2333/245* (2013.01); *G01N 2458/40* (2013.01)
(58) Field of Classification Search
CPC ....... G01N 33/56916; G01N 2333/245; G01N 2458/40
See application file for complete search history.

(56) References Cited

FOREIGN PATENT DOCUMENTS

| EP | 2 682 749 | 1/2014 |
| WO | 2015/075300 | 5/2015 |
| WO | 2015/181546 | 12/2015 |

OTHER PUBLICATIONS

Kulpakko et al. 2019 (Rapid time resolved luminescence based screening of bacteria in urine with luminescence modulating biosensing phages; Analytical Biochemistry 570:21-26) (Year: 2019).*
Kulpakko et al. 2015 (Time-resolved fluorescence-base assay for rapid detection of *E. coli*; Analytical Biochemistry 470: 1-6) (Year: 2015).*
Kulpakko et al., "Rapid time-resolved luminescence based screening of bacteria in urine with luminescence modulating biosensing phages," Analytical Biochemistry, vol. 570, 2019, pp. 21-26.
Masuoka et al., "Zinc(II) and Copper(II) Binding to Serum Albumin, A Comparative Study of Dog, Bovine, and Human Albumin," The Journal of Biological Chemistry, vol. 269, No. 41, Oct. 14, 1994, pp. 25557-25561.
International Search Report for PCT/FI2019/050742 dated Feb. 3, 2020, 3 pages.
Written Opinion of the ISA for PCT/FI2019/050742 dated Feb. 3, 2020, 5 pages.
FI Search Report for FI 20185927 dated May 21, 2019, 2 pages.
Kulpakko et al., "Time-resolved fluorescence-based assay for rapid detection of *Escherichia coli*", Analytical Biochemistry, Feb. 1, 2015, vol. 470, XP055661626, pp. 1-6 (6 total pages).
Burnham et al., "Towards rapid on-site phage-mediated detection of generic *Escherichia coli* in water using luminescent and visual readout", Analytical Bioanalytical Chemistry, Jun. 27, 2014, vol. 406, No. 23, XP035377895, pp. 5685-5693 (10 total pages).
Bardhan et al., "M13 Virus based detection of bacterial infections in living hosts", Journal of Biophotonics, 2013, vol. 7, No. 8, pp. 617-623 (7 total pages).
Farooq et al., "Bacterial biosensing: Recent advances in phage-based bioassays and biosensors", Biosensors and Bioelectronics, Oct. 30, 2018, vol. 118, pp. 204-216 (13 total pages).
Phillips et al. "Rapid and Efficient Identification of Bacteria Using Gold-Nanoparticle-Poly(para-phenyleneethynylene) Constructs", Mar. 2008, vol. 47, No. 14, pp. 2590-2594 (5 total pages).

* cited by examiner

*Primary Examiner* — Mary Maille Lyons
(74) *Attorney, Agent, or Firm* — NIXON & VANDERHYE

(57) ABSTRACT

Disclosed is information related to determining *Escherichia coli* from a sample such as urine. According to the method, part of sample is admixed with a reagent including a lanthanide(III) ion, a transition metal ion, and a transition metal ion/*E. coli*-specific M13 phage, and another part of the sample is admixed with the reagent including lanthanide(III) ion, the transition metal ion a wild-type M13 phage. The signals derived from the lanthanide(III) ions in the admixtures were detected with time-gated luminescence measurement. The presence of *E. coli* in the sample was determined by comparing the lanthanide(III) ion signal in the presence transition metal ion/*E. coli*-specific M13 phage and the wild type M13 phage.

13 Claims, 8 Drawing Sheets

A. B. C.

METHOD FOR DETERMINING ESCHERICHIA COLI

CROSS-REFERENCE TO RELATED APPLICATIONS

This application is the U.S. national phase of International Application No. PCT/FI2019/050742 filed Oct. 17, 2019 which designated the U.S. and claims priority to FI 20185927 filed Nov. 1, 2018, the entire contents of each of which are hereby incorporated by reference.

FIELD

The present invention is related to a method for determining *Escherichia coli* from a sample in particular to a method comprising treating the sample with a reagent comprising a lanthanide(III) ion, transition metal ion and M13 phages.

BACKGROUND

The diagnosis of urinary tract infection (UTI) is based on the clinical symptoms and determination of a causative pathogen. The golden standard for detection and identification of urinary tract pathogen is culture, which enables estimation of the amount of known uropathogenic bacteria in urine. The most common UTI causing pathogen is *Escherichia coli*. Growth of $10^5$ colony forming units (cfu)/mL is the most commonly used cutoff for significant bacteriuria, but depending on the isolated bacteria, patient's symptoms and sampling technique it may be significantly lower. Even with modern media and techniques, urinary cultures create a considerable workload for hospital laboratories. UTIs are very common and therefore also lead to substantial amount of antibiotic prescriptions, some of which could be avoided by faster diagnosis.

Rapid urine tests for UTIs have been developed with aim to reduce laboratory workload. Many of them are based on detecting chemical changes in urine. Leukocyte esterase and nitrite dipstick tests are the most commonly used. Leukocyte esterase leaks from white blood cells to the urine and nitrite is produced mainly from gram-negative bacteria. These two parameters are relatively good indicators when used at the same time. It is recommended that dipstick test results should be considered positive if either parameter was positive. However, current diagnostic guidelines state that nitrite and leukocyte esterase tests are unable to eliminate the possibility of bacterial infection.

Flow cytometry is a convenient method for separating particles in different liquids. In case of urine samples, it can detect bacteria and different blood cell types, most importantly leucocytes. Cytometry alone or used with results of dipsticks does not, however, give accurate prediction of UTI with lower cut-offs ($10^4$ or even $10^3$ CFU/mL) which are applied on primary uropathogens, especially *E. coli*, and certain symptomatic patient groups, the percentage of false-negatives may become high with this method, especially if only bacterial counts are considered. However, with locally validated cutoffs flow cytometry can be used to rule out UTI and reduce the number of samples to be cultivated by up to 50% and thus workload in the lab, as well as shorten the time to a negative result.

Kulpakko et al. [Anal. Biochem. 470 (2015) pp. 1-6] have developed a rapid assay for detecting *E. coli* which is based on lytic phage and bacterial lysis which can be detected via environmentally sensitive lanthanide label. The sensitive label interacts with released molecules from lysed cells. However, specific infection and lysis is a time-consuming process and phage has to be specifically lytic for each bacterial species.

Thus, there is still need for further rapid methods for *E. coli* detection.

SUMMARY

The present invention is based on the observation that *E. coli* can be determined from a sample simply by admixing a first part of the sample with a reagent comprising a lanthanide(III) ion, a transition metal ion, and a M13 phage, and by admixing a second part of the sample with the lanthanide(III) ion, the transition metal ion and wild type M13 phage followed by detecting signal derived from the lanthanide(III) ions from the two admixtures with time-gated luminescence measurement. When the M13 phage has higher affinity towards the transition metal ion and *E coli* than the wild type M13 phage, difference between luminescence signals obtained from the two admixtures is an indication of the presence of *E. coli* in the sample.

According to one aspect the present invention concerns a method for determining *E. coli* in a sample employing at least a first admixture and a first reference admixture, the method comprising following steps:
a) for providing the first admixture, admixing a first part of the sample with
   M13 phage,
   transition metal ion, and
   a reagent comprising lanthanide(III) ion,
b) for providing the first reference admixture, admixing a second part of the sample with
   type M13 phage,
   the transition metal ion,
   the reagent comprising lanthanide(III) ion,
c) detecting at predetermined time point signal derived from the lanthanide(III) ion of the first admixture and signal derived from the lanthanide(III) ion of the first reference admixture with time-gated luminescence measurement,
d) comparing signal derived from the lanthanide(III) ion of the first admixture to the signal derived from the lanthanide(III) ion of the first reference admixture, and
e) determining the *E. coli* in the sample based on the comparing,
in proviso that binding constant of the M13 phage towards the transition metal ion and binding constant of the M13 phage towards *E. coli* is higher than binding constant of the wild type M13 phage towards the transition metal ion and binding constant of the wild type M13 phage towards *E. coli*.

According to another aspect the present invention concerns a kit for determining *E. coli* from a sample, the kit comprising,
   a reagent comprising lanthanide(III) ion,
   a transition metal ion,
   wild type M13 phage and
   M13 phage,
in proviso that binding constant of the M13 phage towards the transition metal ion and binding constant of the M13 phage towards *E. coli* is higher than binding constant of the wild type M13 phage towards the transition metal ion and binding constant of the wild type M13 phage towards *E. coli*.

Further aspects of the present invention are disclosed in the dependent claims.

Exemplifying and non-limiting embodiments of the invention, both as to constructions and to methods of operation, together with additional objects and advantages thereof, are best understood from the following description of specific exemplifying embodiments when read in connection with the accompanying drawings.

The verbs "to comprise" and "to include" are used in this document as open limitations that neither exclude nor require the existence of unrecited features. The features recited in the accompanied depending claims are mutually freely combinable unless otherwise explicitly stated. Furthermore, it is to be understood that the use of "a" or "an", i.e. a singular form, throughout this document does not exclude a plurality.

DESCRIPTION

Figure 1:
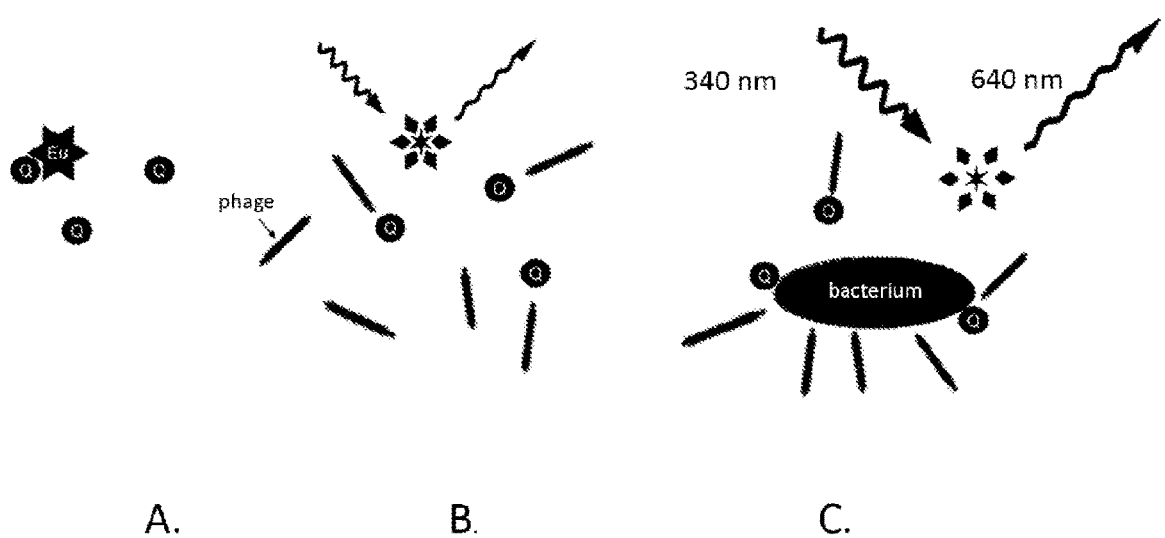
FIG. 1 shows the principle of the present invention; Eu=reagent comprising lanthanide(III) ion; Q=transition metal ion; A=low signal; B=intermediate signal; C=high signal.

The present invention concerns a method for determining *E. coli* from a sample employing at least a first admixture and a first reference admixture. The method comprises following steps:

a) for providing the first admixture, admixing a first part of the sample with
   M13 phage,
   transition metal ion, and
   a reagent comprising lanthanide(III) ion, b) for providing the first reference admixture, admixing a second part of the sample with
   wild type M13
   the transition metal ion,
   the reagent comprising lanthanide(III) ion, c) detecting at predetermined time point signal derived from the lanthanide(III) ion of the first admixture and signal derived from the lanthanide(III) ion of the first reference admixture with time-gated luminescence measurement, d) comparing the signal derived from the lanthanide(III) ion of the first admixture to the signal derived from the lanthanide(III) ion of the first reference admixture, and e) determining the *E. coli* in the sample based on the comparing.

According to the method, affinity of the M13 phage towards the transition metal ion and *E. coli* is higher than the affinity of the wild type M13 phage towards the transition metal ion and *E. coli*.

As defined herein a wild type M13 phage (M13 wt) is a phage that does not interact specifically with transition metal ions, in particular with copper ions and *E coli*. Binding constant of the wild type M13 phage towards $Cu^{2+}$ ions is $10^6$ pfu or less, and towards *E. coli* $10^5$ pfu or less when *E. coli* concentration is $10^4$ cfu.

Wild type M13 phage is any random phage taken from a library that has not undergone any selection phases of the biopanning procedure. Wild type M13 phage is supposed to contain random DNA-sequence. Its binding to copper and *E. coli* clearly less than the binding constant of *E. coli*/transition metal-specific phage. Exemplary differences in the binding constants of wild type M13 phage and biopanned M13 phage towards *E. coli* and copper(II) ions are shown in table 1.

TABLE 1

| Phage | binding constant, *E. coli* | binding constant, $Cu^{2+}$ |
| --- | --- | --- |
| biopanned M13 | $10^8$ pfu/mL | $10^7$ pfu/mL |
| Wild type M13 | $10^5$ pfu/mL | $10^5$ pfu/mL |

The M13 phages suitable for the method of the present invention can be selected by biopanning. The affinities of the biopanned M13 phages towards *E. coli* and transition metal ions is preferably $10^7$ pfu/mL, more preferably at least $10^8$ pfu/mL and most preferably at least $10^9$ pfu/mL. According to an exemplary embodiment affinity of the M13 phage towards transition metal ion and *E coli* is minimum titer of $1.5 \times 10^6$ plaque-forming units/mL when solid transition metal is used and $3 \times 10^6$ plaque-forming units/mL for *E. coli*.

According to a particular embodiment the transition metal is copper. The affinities of the biopanned M13 phages towards copper ion and *E. coli* is preferably $10^7$ pfu/mL more preferably at least $10^8$ pfu/mL most preferably at least $10^9$ pfu/mL. According to an exemplary embodiment affinity of the M13 phage towards copper ion and *E coli* is minimum titer of $1.5 \times 10^6$ plaque-forming units/mL when solid copper is used and $3 \times 10^6$ plaque-forming units/mL for *E. coli*.

Accordingly, affinity of the M13 phage towards the transition metal ion, in particular copper ion, and *E. coli* is at least 100, preferably at least 1000, most preferably at least 10 000 times higher than the affinity of the wild type M13 phage towards the transition metal ion and *E coli*.

It is known that transition metal ions are able to quench luminescence of reagents comprising lanthanide(III) ion, such as lanthanide(III) chelates. This phenomenon was exploited in the present method. Exemplary transition metal ions suitable for the method are $Ni^{2+}$, $Cu^{2+}$, $Hg^{2+}$, $Pb^{2+}$, $Ag^+$, $Cr^{3+}$ and $Fe^{3+}$. A particular transition metal ion is $Cu^{2+}$. The transition metal ions are introduced to the method as salts. An exemplary salt is transition metal halide, such as chloride. An exemplary transition metal salt is chloride salt such as $CuCl_2$.

The method includes a reagent comprising lanthanide(III) ion, such as a lanthanide(III) chelate. The lanthanide is preferably selected from europium, terbium, samarium and dysprosium, preferably from europium and terbium, most preferably europium. A preferable lanthanide(III) chelate is a luminescent lanthanide(III) chelate. Exemplary lanthanide (III) chelates suitable for the method are Eu:TTA:TOPO and Eu:NTA:TOPO. These chelates can be prepared by admixing EuCl$_3$, NTA and TOPO, and EuCl$_3$, TTA and TOPO, respectively. An exemplary molar ratio is 5:3:3 for Eu, NTA/TTA and TOPO respectively.

Another lanthanide(III) chelate suitable for the method is a terpyridine-Eu of formula (I)

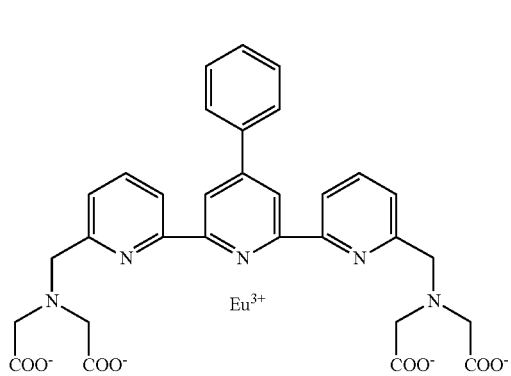

(I)

The method of the present invention is suitable for detecting *E. coli* from a sample, in particular from urine samples. The detection is based on reagent comprising a lanthanide(III) ion in particular to a lanthanide(III) chelate that is sensitive to chemical environment and particularly to transition metals that are able to quench the luminescence of the chelate. The M13 phage in turn interacts both with the metal and the target bacteria. The phage acts as a modulating factor to the achieved time-resolved fluorescence signal. A particular metal is copper as it is well known to quench the fluorescence of lanthanide complexes like Eu$^{3+}$:TTA:TOPO and Eu$^{3+}$:NTA:TOPO.

The principle of the present invention is shown in FIG. 1. In the figure "Q" represents a transition metal ion which is able to quench the luminescence of the lanthanide(III) chelate marked with "Eu". In the absence of M13 phages, the metal ion freely quenches europium signal and a low TRF-signal is detected (A). Higher signal is gained when the metal binding phages are moving randomly in the solution and capturing the quencher (B). When also the target bacteria are present, phages attach not only to the quenchers but also to the bacteria giving rise to even higher TRF-signal (C).

Figure 2:
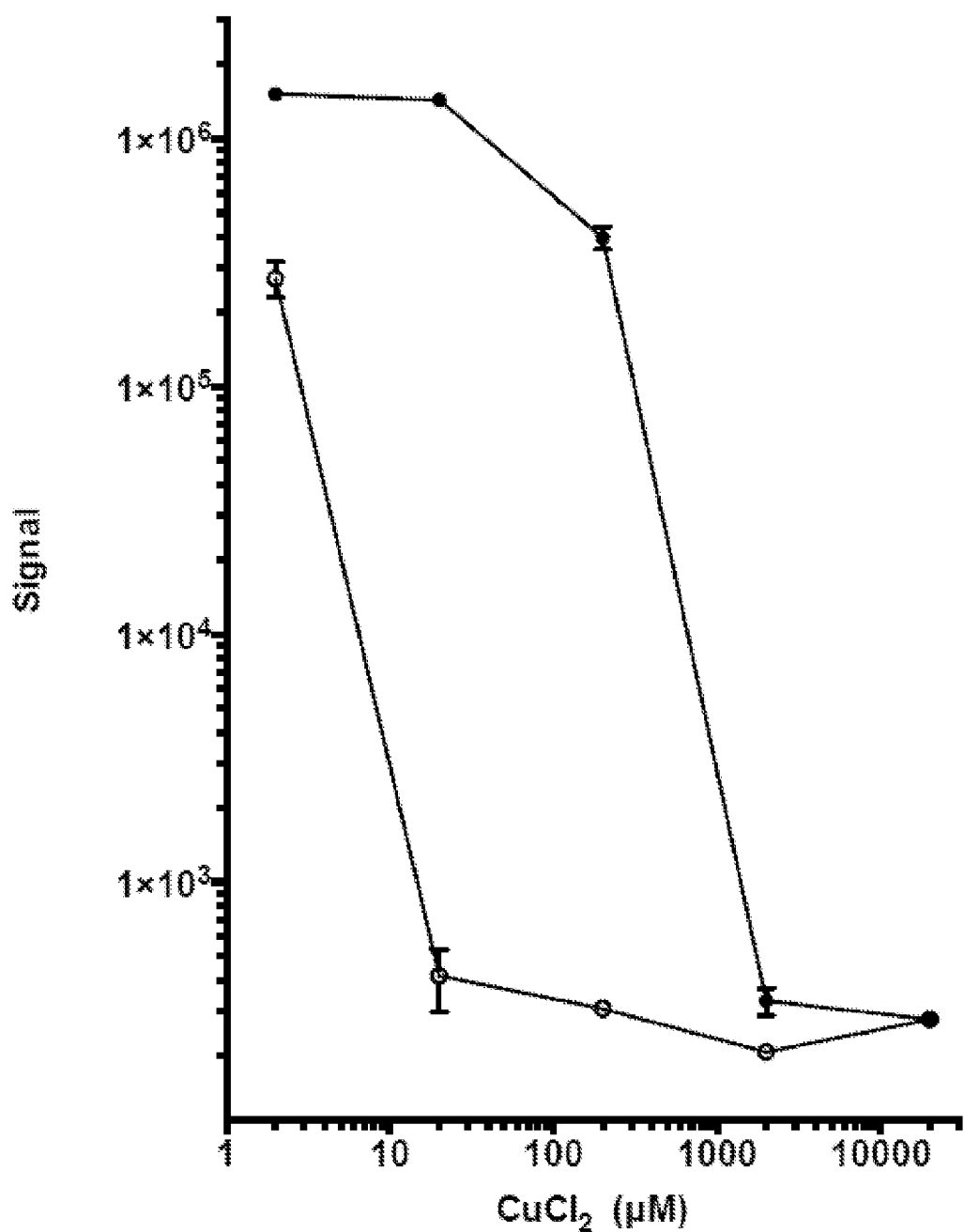
FIG. 2 shows Eu-signal as a function of Cu(II) concentration in the presence of wild type M13 phage (○) and copper/*E. coli*-specific M13 phage (•); Eu chelate Eu:NTA:TOPO.
Figure 3:
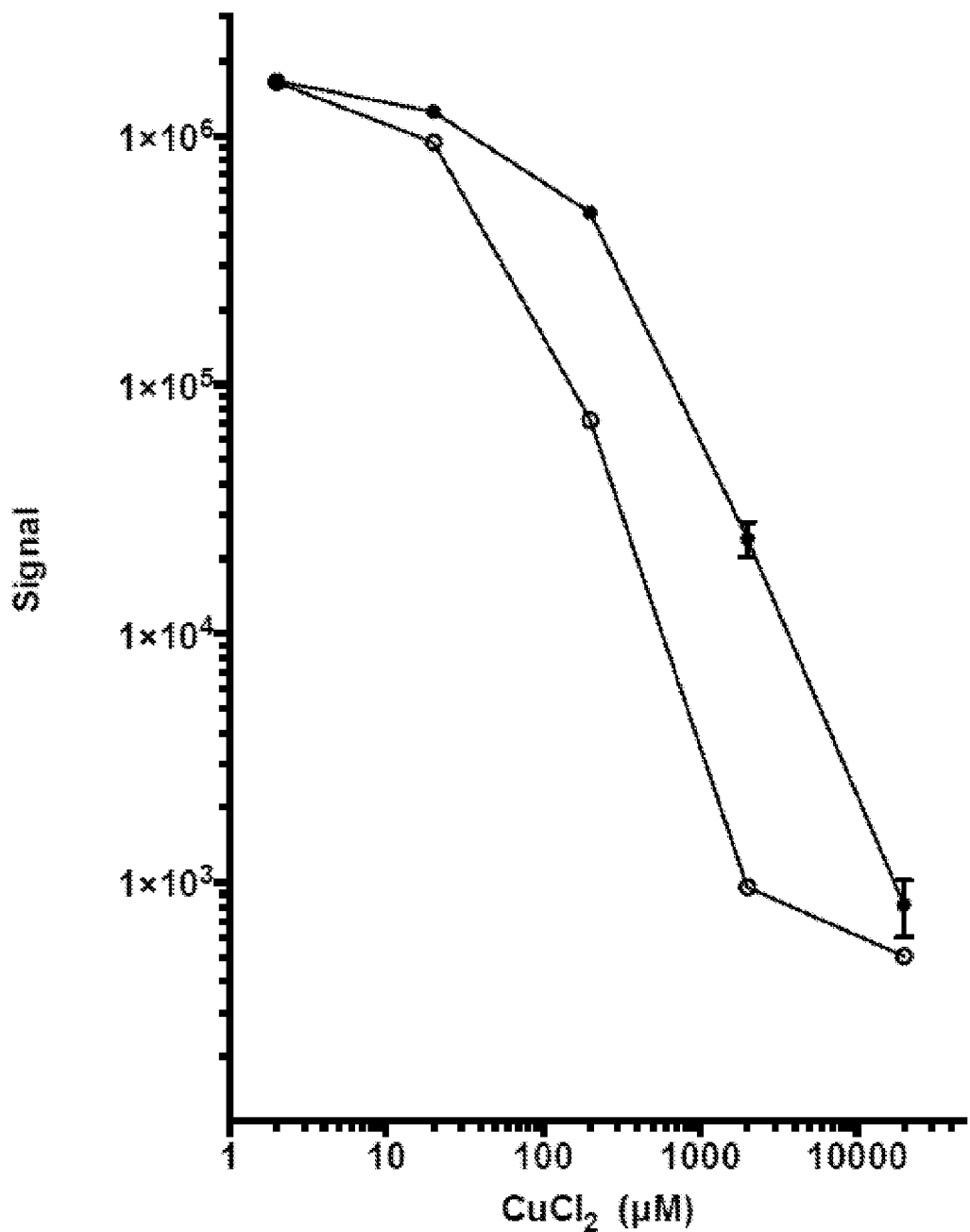
FIG. 3 shows Eu-signal as a function of Cu(II) concentration in the presence of wild type M13 phage (○) and copper/*E. coli*-specific M13 phage (•); Eu chelate terpyridine-Eu.

In order to confirm that M13 phages bind to copper, they were tested in series of different copper chloride concentrations. A comparison was made between wild-type M13 phage and copper/*E. coli* selected M13 phage in the presence of Eu$^{3+}$:TTA:TOPO (FIG. 2) and terpyridine-Eu (FIG. 3). The protocol was first tested with different copper chloride concentrations.

The relative fluorescence signal was higher with copper selective phages M13 than wild type M13 phages. This indicates that under these conditions, copper selective M13 phages protect the lanthanide(III) chelate from quenching. Wild type M13 phage was used throughout the experiments as a control because it was purified with exactly the same procedure as copper/*E. coli* B specific M13 phage. This reduces the possibility that the assay measures irrelevant parameters. In FIGS. 2 and 3, concentration of the wild type M13 phage and copper/*E. coli* B specific M13 phage was 1012 pfu/ml. Among phages the assay reaction also comprised lanthanide(III) chelate and varying amounts of copper chloride (0-20 000 µM). Results were obtained after 10 min incubation.

Figure 4:
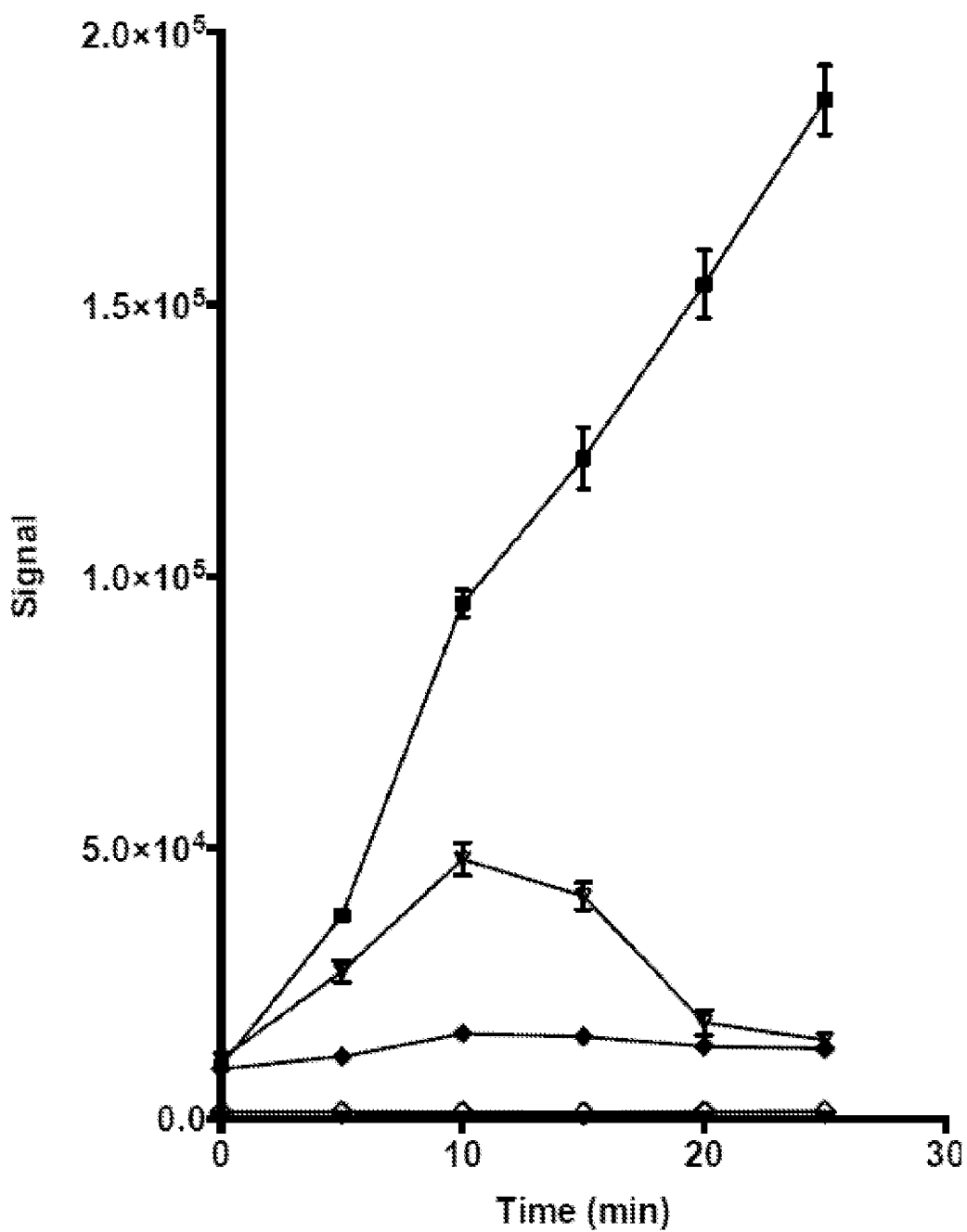
FIG. 4 shows kinetic comparison of copper/*E. coli*-specific M13 phage (■), wild type M13 phage (▼), 0.5% BSA (♦), and control (◇)

FIG. 4 shows Eu signal of Eu$^{3+}$:TTA:TOPO as function of time in the presence 1 µM copper ion and the copper/*E. coli* B specific M13 phage, wild-type M13 phage, BSA and a control (=only Eu$^{3+}$:TTA:TOPO and 1 µM copper ion). After 10 minutes copper/*E. coli* B specific M13 phage continued to protect the chelate from quenching while in the cases of BSA, wild-type M13 phage, and control the relative signal started to decline. BSA is known to bind nonspecific binding sites and metals [Matsuoka et al., J. Biol. Chem. 269 (1994) 41 pp. 25557-25561]. Control phage was not assumed to interfere with copper and results indicate the same.

Figure 6:
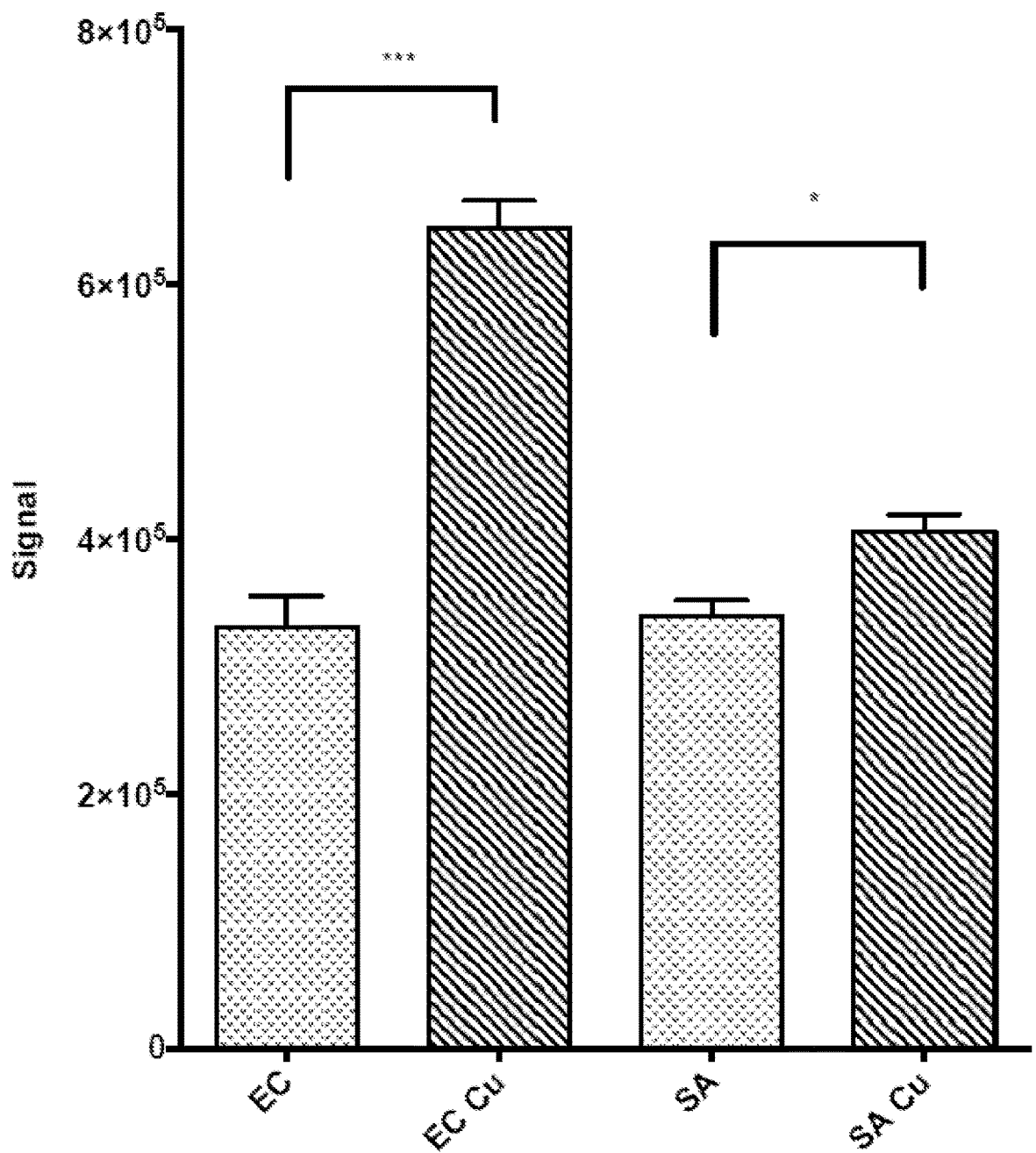
FIG. 6 shows observed time-resolved signal with two different bacterial species in the presence of Cu(II), Eu:TTA:TOPO and the wild type M13 phage or copper/*E. coli*-specific M13 phage.

The assay cross-reactivity was evaluated by comparing *E. coli* and *S. aureus*. As shown in FIG. 6, the copper/*E. coli* B specific M13 phage and wild-type M13 phages have more specificity towards *E. coli*.

According to an embodiment the method utilizes plurality of admixtures and plurality of reference admixtures. According to this embodiment, each admixture and each reference admixture comprise the reagent comprising lanthanide(III) ion such as Eu:TTA:TOPO, and a transient metal ion, such as Cu(II) ion. Each admixture comprises copper/*E. coli* B specific M13 phage, and each reference admixture comprises a wild-type M13 phage.

According to a preferable embodiment, each admixture and each reference admixture comprise also one or more modulating agents. A suitable modulating agent has affinity towards one or more of the reagent comprising lanthanide(III) ion
the transient metal ion and
copper/*E. coli* B specific M13 phage and
the wild-type M13 phage.

The modulating agent changes the chemical environment of the admixtures and the reference admixtures and enhances sensitivity and selectivity of the method. Exemplary modulating agent are listed in table 2. Also, exemplary modulator agent concentrations suitable for the method are given.

TABLE 2

| Chemical (supplier, #product code) | Concentration |
|---|---|
| Diethyl malonate, Sigma-Aldrich #D97754 | 20 mM |
| 2,3-Dichloro-5,6-dicyano-p-benzoquinone, Sigma-Aldrich #D60400 | 1.7 mM |
| Triisopropylsilane, Sigma-Aldrich # | 20 mM |
| 1-Bromonaphthalene, Sigma-Aldrich #B73104 | 50 µM |
| Calmagite, Sigma-Aldrich #C204 | 200 µM |
| Chloranil, Sigma-Aldrich #45374 | 4 mM |
| 1,10-Phenanthroline monohydrate, Sigma-Aldrich #P9375 | 15 µM |
| Toluidine Blue O, Sigma-Aldrich #T3260 | 100 µM |
| Crystal Violet, Sigma-Aldrich #C6158 | 120 µM |
| Murexide, Sigma-Aldrich #222461 | 35 µM |
| 8-anilino-1-naphtalene sulfonic acid, Sigma-Aldrich #139920 | 160 µM |
| Benzoyl peroxide, Sigma-Aldrich #8.01641 | 40 µM |
| Creatine hydrate, Sigma-Aldrich #855243 | 800 µM |
| 2-Furoyl chloride, Sigma-Aldrich #149861 | 700 µM |
| N-hydroxysuccinimide, Sigma-Aldrich #130672 | 4 mM |
| N-Bromosuccininnide, Sigma-Aldrich #681255 | 800 µM |
| 2,4,6-Tribromo-3-hydroxybenzoic acid, Sigma-Aldrich #439533 | 80 µM |
| Malachite Green chloride, Sigma-Aldrich #38800 | 5 µM |
| Eosin B, Sigma-Aldrich #861006 | 700 µM |
| Safarin O, Sigma-Aldrich #S2255 | 100 µM |

According to an exemplary embodiment, the method comprises four admixtures and four reference admixtures, namely first admixture, first reference admixture, second admixture, second reference admixture, third admixture, third reference admixture, fourth admixture and fourth reference admixture. All admixtures and all reference admixtures comprise the same reagent comprising lanthanide(III) ion such as Eu:NTA:TOPO, and the same transition metal ion such as Cu(II). The admixtures and the reference admixtures comprise the copper/*E. coli* specific M13 phage and wild-type M13 phage, respectively. The admixtures and the reference admixtures comprise also one or more modulating agents. For example, the first admixture and the first reference admixture comprise modulating agent A, the second admixture and the second reference admixture comprise modulating agent B, etc. It is also possible that one or more of the admixtures and reference admixtures comprise plurality of modulating agents. For example, the first admixture and the first admixture comprise modulating agents A, C, and D, and the second admixture and the second reference admixture comprise modulating agent B, etc. The plurality of reference admixtures produces a fingerprint of the sample in the presence of wild-type M13 phage and the plurality of admixtures produces a fingerprint of the sample in the presence of copper/*E. coli* specific M13 phage. *E. coli* is then determined by comparing TRF signals obtained from these two fingerprints.

Figure 7:
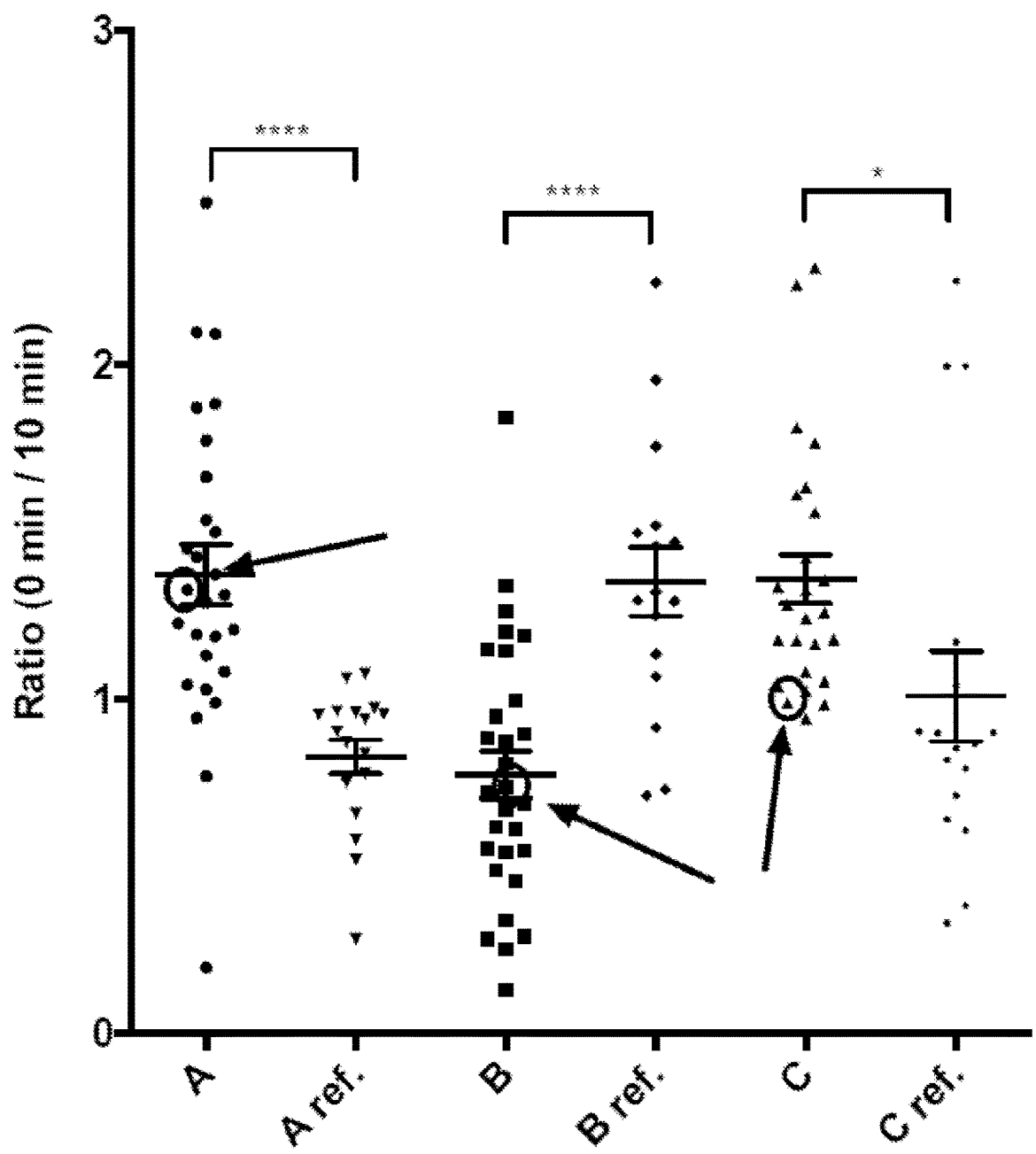
FIG. 7 shows screening of patient samples with the method of the present invention [transition metal ion=Cu (II); reagent comprising lanthanide(III) ion=Eu:TTA:TOPO modulating agent: (A) diethyl malonate, (B) 2,3-dichloro-5,6-dicyano-p-benzoquinone, (C) triisopropylsilane]

FIG. 7 presents screening of urine samples in three chemical environments using diethyl malonate (A), 2,3-dichloro-5,6-dicyano-p-benzoquinone (B) and triisopropylsilane (C) as modulating agents. Each sample was divided in three 100 μL replicates for wild-type M13 phage and copper/*E. coli* B specific M13 phage. Since three chemical environments were utilized, the obtained data was analyzed with K-Nearest Neighbor (KNN) classification method.

Since the response differed between these chemistries (increase/decrease/magnitude) it can be assumed that each of the three modulator agents reveal varying properties of the sample-chelate interaction. Using the three different chemical environments resulted improved the classification precision.

The KNN method was taught by using artificial random noise contaminated averages for each of the categories. The algorithm classified *E. coli* from sample data with the output of 90% sensitivity and specificity. This is a competitive result when compared with other rapid screening methods for urine. Comparing the categories in FIG. 7, it is evident, that although the differences between reference and *E. coli* patient samples was in all cases significant, using a simple cut-off value would have not reached the same 90% mark as was reached with fingerprinting and the K-Nearest neighbor algorithm. Furthermore, as shown in the figure, a single sample (circled in the FIG. 7) which would have been misclassified using triisopropylsilane as the modulator agent was correctly classified by KNN and the two other modulating agents.

The experiment shown in FIG. 7 comprises 70 patient urine samples, five of which had turbidity or reddish color. This is likely due to red blood cells leaking from urinary tract system and precipitation of salts. All these samples were correctly classified by KNN algorithm.

*E. coli* is by far the most prevalent causative agent in urinary tract infection. The assay sensitivity and specificity reached with the method of the present invention is at the same level as current flow cytometric and dipstick methods. The limit of detection was in the range of clinical level (<10 000 cfu/mL). The results could be obtained in 10 minutes from the time reaction was started. Urine samples were not treated before screening them. Nonetheless, this didn't cause interference to the method and clear cross-reactivity to other bacterial species was not seen.

According to another embodiment the present invention concerns a kit for determining *E. coli* from a sample such as urine, the kit comprising
 a reagent comprising lanthanide(III) ion,
 a transient metal ion, preferably $Cu^{2+}$,
 wild type M13 phage, and
 M13 phage,
wherein affinity of the M13 phage towards the transient metal ion and the *E coli* is higher than affinity of the wild type M13 phage towards the transient metal ion and the *E coli*.

The binding constant of the wild type M13 phage towards $Cu^{2+}$ ions is $10^6$ pfu or less, and towards *E. coli* $10^5$ pfu or less when *E. coli* concentration is $10^4$ cfu.

According to a preferable embodiment affinity of the M13 phage towards the transition metal ion and *E. coli* is at least 100 times, preferably at least 1000 times, most preferably at least 10 000 times higher than the affinity of the wild type M13 phage towards the transition metal ion and *E. coli*.

According to a preferable embodiment the binding constant of the M13 phage towards the transition metal ion is at least titer of $1.5 \cdot 10^6$ plaque-forming units/mL when solid transition metal is used, and binding constant of the M13 phage towards *E. coli* is at least titer of $3 \cdot 10^6$ plaque-forming units/mL, preferably at least titer of $2 \cdot 10^8$ plaque-forming units/mL.

According to a preferable embodiment the kit comprises also one or more modulating agents, wherein the one or more modulating agent have affinity towards one or more of
 the reagent comprising lanthanide(III) ion,
 the transient metal ion,
 the wild type M13 phage, and
 the M13 phage.

The reagent comprising lanthanide(III) ion is preferably a lanthanide(III) chelate preferably selected from Eu:TTA:TOPO, Eu:NTA:TOPO and terpyridine-Eu of formula (I).

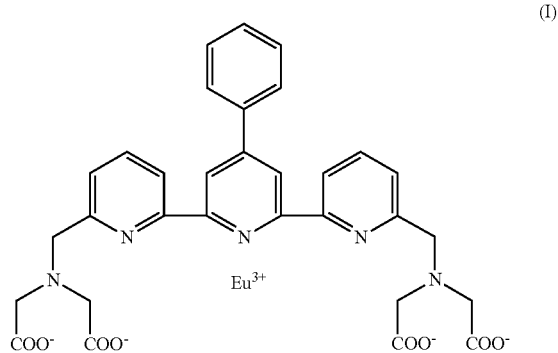

(I)

The one of more modulating agents are preferably selected from the group consisting of diethyl malonate, 2,3-dichloro-5,6-dicyano-p-benzoquinone, triisopropylsilane, 1-bromonaphthalene, calmagite, chloranil, 1,10-phenanthroline monohydrate, toluidine blue O, crystal violet, murexide, 8-anilino-1-naphthalene sulfonic acid, benzoyl peroxide, creatine hydrate, 2-furoyl chloride, N-hydroxysuccinimide, N-bromosuccinimide, 2,4,6-tribromo-3-hydroxybenzoic acid, malachite green chloride, eosin B, and safarin O, preferably diethyl malonate, 2,3-dichloro-5,6-dicyano-p-benzoquinone, triisopropylsilane.

Materials and Methods

Samples 70 clinical samples were analyzed and cultured at Clinical Microbiology Laboratory of Turku University Central Hospital. Samples were collected in vacutainer Plus C&S boric acid sodium borate/formate tubes (Becton Dickinson). Clearly bloody or smear samples were not excluded from analysis. The urine samples were stored at 4° C. Ethical approval for using the patient samples was not required for the reason that the study was considered as a basic laboratory screening method development and no additional patient information was collected. Microorganisms identified from the samples are shown in table 3.

TABLE 3

| Microorganism | CFU Count/mL | No. of Cases |
|---|---|---|
| Escherichia coli | $\geq 10^3$ | 29 |
| negative | — | 14 |
| Klebsiella pneumoniae | $\geq 10^3$ | 5 |
| Enterococcus faecalis | $\geq 10^5$ | 4 |
| Citrobacter freundii | $\geq 10^5$ | 3 |
| Proteus mirabilis | $\geq 10^4$ | 2 |
| Citrobacter koseri | $\geq 10^3$ | 2 |
| Pseudomonas aeruginosa | $\geq 10^4$ | 2 |
| enterococcus (non-faecalis species) | $\geq 10^3$ | 2 |
| Hafnia alvei | $\geq 10^5$ | 1 |
| Streplococcus agalactiae | $\geq 10^5$ | 1 |
| Pseudomonas putida | $\geq 10^5$ | 1 |
| Staphylococcus saprophyticus | $\geq 10^5$ | 1 |
| Staphylococcus hominis | $\geq 10^5$ | 1 |
| Raoultella ornithinolytica | $\geq 10^3$ | 1 |

Materials and Reagents

Yeast-Tryptone (YT) medium was made of mixing 16 g of tryptone, 10 g of yeast extract and 5 g of NaCl to one liter of MQ water. Diethyl malonate, Bovine Serum Albumin (BSA), Europium (III) chloride hexahydrate, 2,3-Dichloro-5,6-dicyano-p-benzoquinone and (TOPO) tri-n-octyl-phosphine oxide were purchased from Sigma-Aldrich.

Triisopropylsilane was purchased from Fluka, Buchs, Switzerland and (NTA) 4,4,4-trifluoro-1-(2-naphthalenyl)-1,3-butanedione (NTA) and 2-thenoyltrifluoroacetone (TTA) from Acros Organics. Dimethyl sulfoxide, analytical reagent grade (DMSO) was purchased from Thermo Fisher Scientific, MA, USA. The bacterial reference strains used in the development of the assay were: Staphylococcus aureus ATCC 25923 and E. coli strain B ATCC 11303 as a reference of wild type E. coli because it has no F plasmids that M13 phage requires for infection process.

Biopanning

Figure 8:
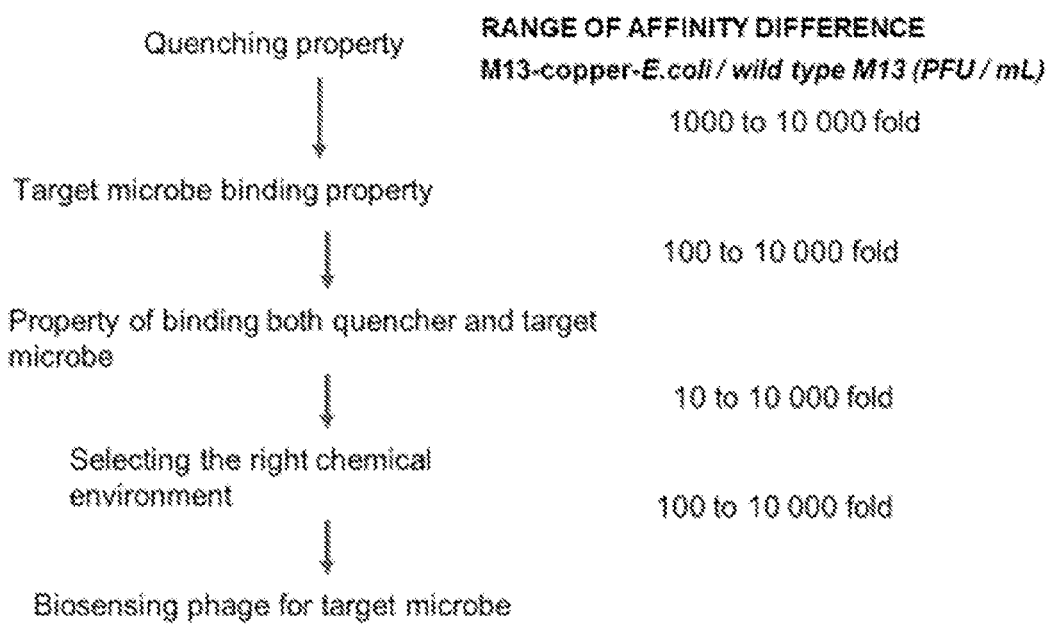
FIG. 8 shows the overall schematics to produce biosensing phage that is used in the method of the present invention.

The method of the present invention utilized a M13 phage which has higher affinity towards the transition metal ion and E coli than wild-type M13 phage. The overall schematics to produce a biosensing phage that is functioning in the method is described in FIG. 8. Furthermore, it indicates acceptable affinity ranges in each stage of the system. The affinity is shown as M13-copper-E. coli with biosensing properties compared to wild type M13 phage (pfu/mL).

Library Screenings

First Affinity Screening Procedure for Copper

Figure 5:
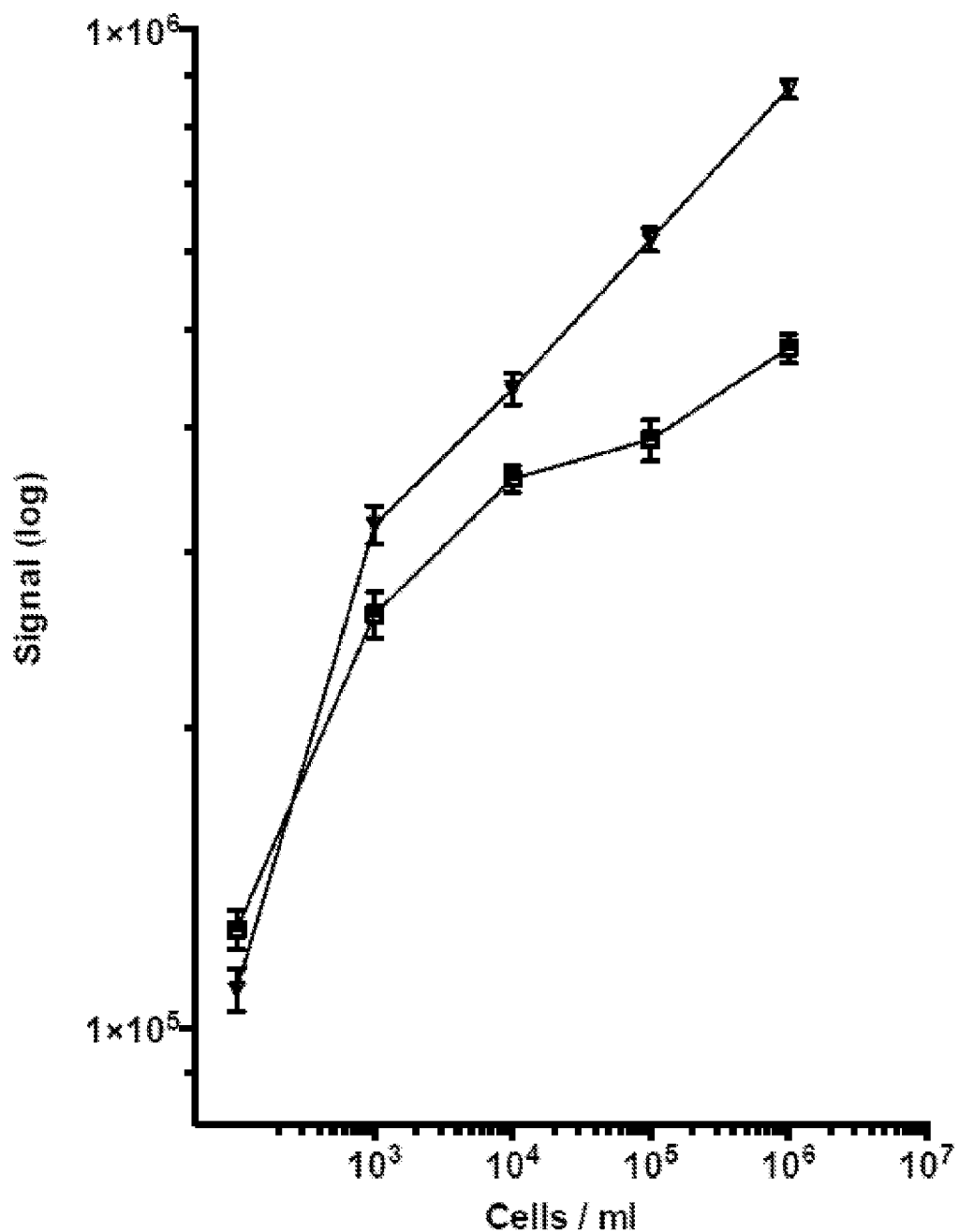
FIG. 5 shows log of Eu signal obtained in the presence of copper/*E. coli*-specific M13 phage (▼) and wild type M13 phage (■) as a function of *E. coli* concentration.

First phase of creating biosensing phage is to go over biopanning procedure with copper. Even slight phage affinity towards copper is observable with the assay deploying TRF instrument (FIG. 5). Copper beads (Sigma Aldrich 254177, 2-8 mm) were rinsed with distilled water and autoclaved 120° C. for 60 min before the biopanning experiments. The selected biopanning system, The Ph.D.-12 phage display peptide library (E8110S) was supplied by New England Biolabs (NEB). The library contains $1.5 \times 10^{13}$ plaque-forming units (pfu)/ml and it has complexity of $2 \times 10^9$ independent peptide sequences. Each phage contains five copies of the minor coat protein pIII, and each copy of pIII has a single peptide displayed at its N-terminus. Suitable strain E. coli ER2738 containing the F+Δ(lacZ)M15 plasmid (New England Biolabs) was used to amplify the eluted phage. LB medium was used to culture E. coli. To prevent contaminating phage from the environment, eluted phage was plated on LB agar plates containing 60 μg/ml isopropyl β-D-thiogalactoside (IPTG) and 40 μg/mL 5-bromo-4-chloro-3-indolyl-β-D-galactoside (Xgal). Biopanning was performed following a modified protocol from New England Biolabs. An 10 μl aliquot of the random peptide library was incubated with a copper beads at RT for 30 min with gentle shaking in a microcentrifuge tube containing 1 mL of physiological saline. Unbound phage from metal beads was washed serially with 4 mL of TBST-buffer [0.1% (v/v) Tween-20 in TBS (50 mM Tris-HCl, pH7.5, 150 mM NaCl)]. After the 15 washes, the bound phage was eluted with 1 ml of 0.2 M glycine-HCl (pH 2.2). In each round, the bound phages were rescued and amplified using E. coli ER2738 to make more copies. Phage clones are saved for testing affinity and frozen −70° C. for possible sequencing and sequence comparison. These were used in a second round of biopanning. After three rounds of biopanning (three rounds of 15 washes) the bound phages were harvested for binding analysis. Chosen phages had properties capable of binding copper with minimum titer of $1.5 \times 10^8$ plaque-forming units and capable of propagating in E. coli ER2738.

Second Affinity Screening Procedure for E. coli B

Enriched phages from previous screening were used for biopanning experiments against E. coli B. Purpose of this biopanning phase is to have affinity against target bacteria without losing too much already obtained affinity towards transition metal quencher. This will be tested with several independent clones obtained from the experiments.

The panning procedure was performed according to the following protocol: E. coli B cells were grown in tryptic soy broth (TSB; Sigma-Aldrich) medium at 37° C. The growth medium was centrifuged, and the pellet washed twice with 1 mL of 4° C. PBST (Phosphate Buffered Saline with Tween 20). The random peptide library ($1.5 \times 10^{11}$ plaque-forming units) was mixed with washed cells and incubated in 1% BSA (Bovine serum albumin) with the washed infectious E. coli B cells and left on ice for 1 h. After this phage bound cells were washed twice with 1 mL PBST and three times 1 mL PBS. Washed cells were mixed with 1 mL of phage propagating E. coli ER2738 ($1.0 \times 10^9$ cells/mL) in 2×YT medium. Before mixing E. coli ER2738 cells were grown in intense shaking (250 rpm) at 37° C. The mixed culture of E. coli ER2738 and E. coli B was incubated for 30 min at 37° C. without shaking and following an incubation period of 30 min with gentle shaking (100 rpm). The enrichment of phages was made according to the manufacturer's protocol (NEB). After third affinity selection phages were ready for to be used in assays. Chosen phages had properties capable of binding copper with minimum titer of $1.5 \times 10^6$ plaque-forming units/mL, and capable of propagating normally in E. coli ER2738. Secondly, phages had properties capable of binding E. coli with minimum titer of $3 \times 10^6$-$3 \times 10^8$ plaque-forming units/mL.

Wild type phage used has random 12-mer peptides fused to a minor coat protein (pIII) of M13 phage. Basic structure of the wild type phage does not differ from the selected M13-copper-*E. coli* phage. Only difference is the order of amino acids in the minor coat protein and hence the order of DNA-sequence. The DNA-sequence for functioning biosensing assay can be various combinations of nucleotides.

Selecting the Right Chemical Environments

Each chemical environment consisting a reagent comprising a lanthanide(III) ion, copper chloride and wild type M13 phage or copper/*E. coli*-specific M13 phage was added 4 μL chemical investigated. A result that enhances copper/*E. coli*-specific M13 phages signal more than 2-fold compared to situation where wild type M13 was present and was selected for final assay setup.

Copper Binding Experiments

Tested copper chloride concentration (0-200 mM) in MQ was added in 100 μL volume to 96 well plate. Then each well was added 1012 pfu/mL M13 wild-type (wt-m13) phage or copper selected phage in volume of 10 μL. Finally, 4 μL of 0.1 mM europium chloride, 0.06 mM NTA and 0.06 mM TOPO was added to the microtiter wells. After 10 minutes of incubation, delayed luminescence emission intensities were measured in a 400 μs window after a 400 μs delay time using a Victor 2 multilabel counter (Wallac, Perkin Elmer Life and Analytical Sciences).

Assay for *E. coli* B and Comparison with *S. aureus*

A 96 well plate was filled with 100 μL of varying concentrations (0-106 cfu/mL) of *E. coli* in physiological saline and after this 8 μL of 20 μM copper chloride in MQ was added. Next each well was added 1013 pfu/ml wt-m13 phage or copper/*E. coli* B selected phage in volume of 10 μL. Finally, 4 μL of 0.1 mM europium chloride, 0.06 mM NTA and 0.06 mM TOPO was added to the microtiter wells. After 10 minutes of incubation, modulated delayed europium luminescence emission intensities were measured again in a 400 μs window after a 400 μs delay time using a Victor 2 multilabel counter. Comparison with *S. aureus* and *E. coli* was done with the same protocol but only one concentration of 1 μM copper chloride was used. Finally, 4 μL of 0.1 mM europium chloride, 0.06 mM NTA and 0.06 mM TOPO was added to the microtiter wells. After 10 minutes of incubation, luminescence emission intensities were measured in a 400 μs window after a 400 μs delay time using a Victor 2 multilabel counter.

Screening Clinical Urine Samples

A 96 well plate was filled with 100 μL of urine sample and right after this, 10 μl of 1013 pfu/ml M13-wt phages or copper/*E. coli* B selected M13 phages and 8 μL of 20 μM copper chloride in MQ was added. Next 4 μL one of three additional chemicals in DMSO were added (600 mM of diethyl malonate, 50 mM of 2,3-dichloro-5,6-dicyano-p-benzoquinone or 600 mM triisopropylsilane). Finally, 4 μl of 0.1 mM europium chloride, 0.06 mM NTA and 0.06 mM TOPO was added to the microtiter wells. After 10 minutes of incubation, luminescence emission intensities were measured in a 400 μs window after a 400 μs delay time using a Victor 2 multilabel counter.

Statistical Analysis

The samples were analyzed in three chemical environments and with two different phage types: *E. coli* B/copper specific M13 phage and reference M13 phage. In the analysis the signal from time point 0 min was compared with that of 10 min. This was done to compensate the possible variations in the signal due to unrelated matrix variations. The aim was to obtain and evaluate the statistical difference in signal between *E. coli* and other samples. These include 14 other bacterial species representing both known uropathogens and normal microbiota of the urogenital area, and negative samples. High signal difference between specific and reference phage indicated positive result for *E. coli* in urine sample, whereas small signal difference indicated the negative result for *E. coli*. For screening assay, all selected three chemistries were used as a fingerprint of the sample. The used classification method was K-Nearest Neighbor (KNN), and the averages from each of the class, contaminated with random noise of amplitude equivalent to the noise in the real data, were used in teaching of the algorithm. The KNN analysis was performed with Molegro Data Modeler (Version 2.1), and all plotting and statistics with Prism 6.0 g.

The specific examples provided in the description given above should not be construed as limiting the scope and/or the applicability of the appended claims. Lists and groups of examples provided in the description given above are not exhaustive unless otherwise explicitly stated.

What is claimed is:

1. A method for determining *Escherichia coli* (*E. coli*) in a urine sample employing at least a first admixture and a first reference admixture, the method comprising the following steps:
    a) for providing the first admixture, admixing a first part of the sample with
        M13 phage,
        $Cu^{2+}$ion, and
        a reagent comprising a europium (III) ion,
    b) for providing the first reference admixture, admixing a second part of the sample with
        a wild type M13 phage,
        the $Cu^{2+}$ion,
        the reagent comprising a europium (III) ion,
    c) detecting at a predetermined time point, a signal derived from the europium (III) ion of the first admixture and a signal derived from the europium (III) ion of the first reference admixture with time-gated luminescence measurement,
    d) comparing the signal derived from the europium (III) ion of the first admixture to the signal derived from the europium (III) ion of the first reference admixture, and
    e) determining the *E. coli* in the sample based on the comparing, in proviso that
        the binding constant of the M13 phage toward the $Cu^{2+}$ion is larger than the binding constant of the wild type M13 phage towards the $Cu^{2+}$ion;
        the binding constant of the M13 phage toward the *E. coli* is larger than the binding constant of the wild type M13 phage towards *E. coli*;
        the *E. coli* concentration in the urine sample is at least $10^3$ cells/mL;
        the $Cu^{2+}$concentration in the first reference admixture does not exceed 1000 μM; and
        the $Cu^{2+}$concentration in the first admixture does not exceed 1000 μM.

2. The method according to claim 1, wherein the binding constant of the wild type M13 phage towards $Cu^{2+}$ions is $10^6$ plaque-forming units/mL or less, and towards *E. coli* is $10^5$ plaque-forming units/mL or less when *E. coli* concentration is $10^4$ colony-forming units/mL.

3. The method according to claim 1, wherein the binding constant of the M13 phage towards the $Cu^{2+}$ion is at least a titer of $1.5 \cdot 10^6$ plaque-forming units/mL when solid copper is used, and the binding constant of the M13 phage towards *E. coli* is at least a titer of $3 \cdot 10^6$ plaque-forming units/mL.

4. The method according to claim 1, wherein step a) and step b) comprise admixing with one or more modulating agents wherein the one or more modulating agents have affinity towards one or more of the reagent comprising europium (III) ion,
the $Cu^{2+}$ ion,
the M13 phage, and
the wild type M13 page.

5. The method according to claim 4, wherein the one or more modulating agents is selected from a group consisting of diethyl malonate, 2,3-dichlro-5,6-dicyano-p-benzoquinone, triisopropylsilane, 1-bromonaphthalene, calmagite, chloranil, 1,10-phenanthroline monohydrate, toluidine blue O, crystal violet, murexide, 8-anilino-1-naphthalene sulfonic acid, benzoyl peroxide, creatine hydrate, 2-furoyl chloride, N-hydroxysuccinimide, N -bromosuccinimide, 2,4,6-tribromo-3-hydroxybenzoic acid, malachite green chloride, eosin B, and safarin O.

6. The method according to claim 1, wherein the reagent comprising europium (III) ion is a europium (III) chelate, and the europium (III) chelate is selected from $Eu^{3+}$:TTA:TOPO, $Eu^{3+}$:NTA:TOPO and terpyridine-Eu of formula (I):

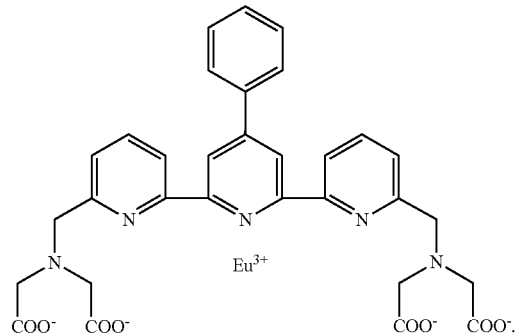

(I)

7. A kit for determining *Escherichia coli* (*E. coli*) from a urine sample, the kit comprising:
a reagent comprising europium (III) ion,
$Cu^{2+}$ ion,
wild type M13 phage, and
M13 phage,
wherein affinity of the M13 phage towards the $Cu^{2+}$ ion and the *E. coli* is higher than affinity of the wild type M13 phage towards the $Cu^{2+}$ ion and the *E. coli*.

8. The kit according to claim 7 wherein the binding constant of the wild type M13 phage towards $Cu^{2+}$ ions is $10^6$ plaque-forming units/mL or less, and towards *E. coli* is $10^5$ plaque-forming units/mL or less when *E. coli* concentration is $10^4$ colony-forming units/mL.

9. The kit according to claim 7 further comprising one or more modulating agents, wherein the one or more modulating agents have affinity towards one or more of
the reagent comprising europium (III) ion,
the $Cu^{2+}$ ion,
the wild type M13 phage, and
the M13 phage.

10. The kit according to claim 7, wherein the reagent comprising europium (III) ion is a europium (III) chelate selected from Eu:TTA:TOPO, Eu:NTA:TOPO and terpyridine-Eu of formula (I):

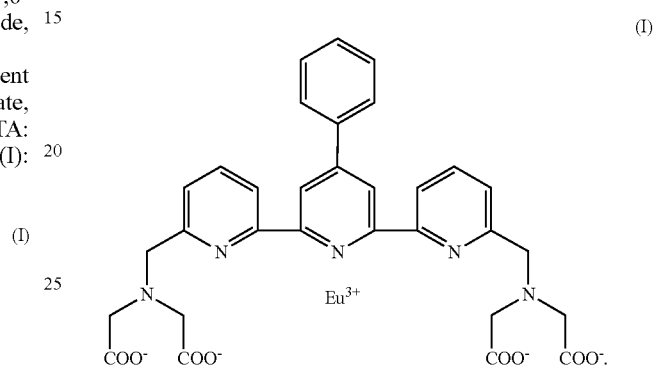

(I)

11. The kit according to claim 9, wherein the one of more modulating agents are selected from the group consisting of diethyl malonate, 2,3-dichloro-5,6-dicyano-p-benzoquinone, triisopropylsilane, 1-bromonaphthalene, calmagite, chloranil, 1,10-phenanthroline monohydrate, toluidine blue O, crystal violet, murexide, 8-anilino-1-naphthalene sulfonic acid, benzoyl peroxide, creatine hydrate, 2-furoyl chloride, N-hydroxysuccinimide, N -bromosuccinimide, 2,4,6-tribromo-3-hydroxybenzoic acid, malachite green chloride, eosin B, and safarin O.

12. The kit according to claim 7, wherein the binding constant of the M13 phage towards the $Cu^{2+}$ ion is at least a titer of $1.5 \cdot 10^6$ plaque-forming units/mL when solid copper is used, and the binding constant of the M13 phage towards *E. coli* is at least a titer of $3 \cdot 10^6$ plaque-forming units/mL.

13. The kit according to claim 7, wherein affinity of the M13 phage towards the $Cu^{2+}$ ion and *E. coli* is at least 100 times higher than the affinity of the wild type M13 phage towards the $Cu^{2+}$ ion and *E. coli*.

\* \* \* \* \*